United States Patent [19]

White

[11] Patent Number: 4,806,863
[45] Date of Patent: Feb. 21, 1989

[54] EDDY CURRENT APPARATUS INCLUDING CYLINDRICAL COIL WITH FLUX CONCENTRATOR FOR HIGH RESOLUTION DETECTION OF FLAWS IN CONDUCTIVE OBJECTS

[75] Inventor: John K. White, Bethel Park, Pa.

[73] Assignee: Westinghouse Electric Corp., Pittsburgh, Pa.

[21] Appl. No.: 919,944

[22] Filed: Oct. 17, 1986

[51] Int. Cl.⁴ .................. G01N 27/82; H01F 3/00; H01F 17/04
[52] U.S. Cl. .................. 324/238; 324/220; 336/132; 336/134; 336/221
[58] Field of Search .................. 324/219–221, 324/228–243; 376/249, 250, 251, 254; 336/132, 134, 221

[56] References Cited

U.S. PATENT DOCUMENTS

| | | | |
|---|---|---|---|
| 2,104,644 | 1/1938 | Greenslade | 324/219 |
| 3,114,876 | 12/1963 | Schuster | 324/221 X |
| 3,116,452 | 12/1963 | Schmidt | 324/40 |
| 3,535,623 | 10/1970 | Wood et al. | 324/37 |
| 3,754,275 | 8/1973 | Carter et al. | 346/1 |
| 3,845,381 | 10/1974 | Hart | 324/221 |
| 3,878,453 | 4/1975 | Potter et al. | 324/3 |
| 4,002,967 | 1/1977 | Fennell | 324/238 |
| 4,088,953 | 5/1978 | Sarian | 324/232 |
| 4,203,069 | 5/1980 | Davis | 324/220 |
| 4,204,159 | 5/1980 | Sarian et al. | 324/232 |
| 4,502,006 | 2/1985 | Goodwin et al. | 324/234 X |
| 4,507,610 | 3/1985 | Nakaoka | 324/238 |
| 4,629,984 | 12/1986 | Scalese | 324/228 |
| 4,659,990 | 4/1987 | Torre | 324/238 |

FOREIGN PATENT DOCUMENTS 627393 8/1978 U.S.S.R.

*Primary Examiner*—Gerard R. Strecker

[57] ABSTRACT

Apparatus for testing for flaws in conductive objects which includes a coil of electrically conducting wire and an associated flux concentrator of electromagnetically active material which is disposed radially from the coil, sized and shaped to provide a desired resolution of flaw detection and provides close coupling between the coil and conductive object. An associated bridge circuit detects changes in the coil's impedance, caused by flaws in the object, and activates a display to visually indicate a change in impedance.

13 Claims, 4 Drawing Sheets

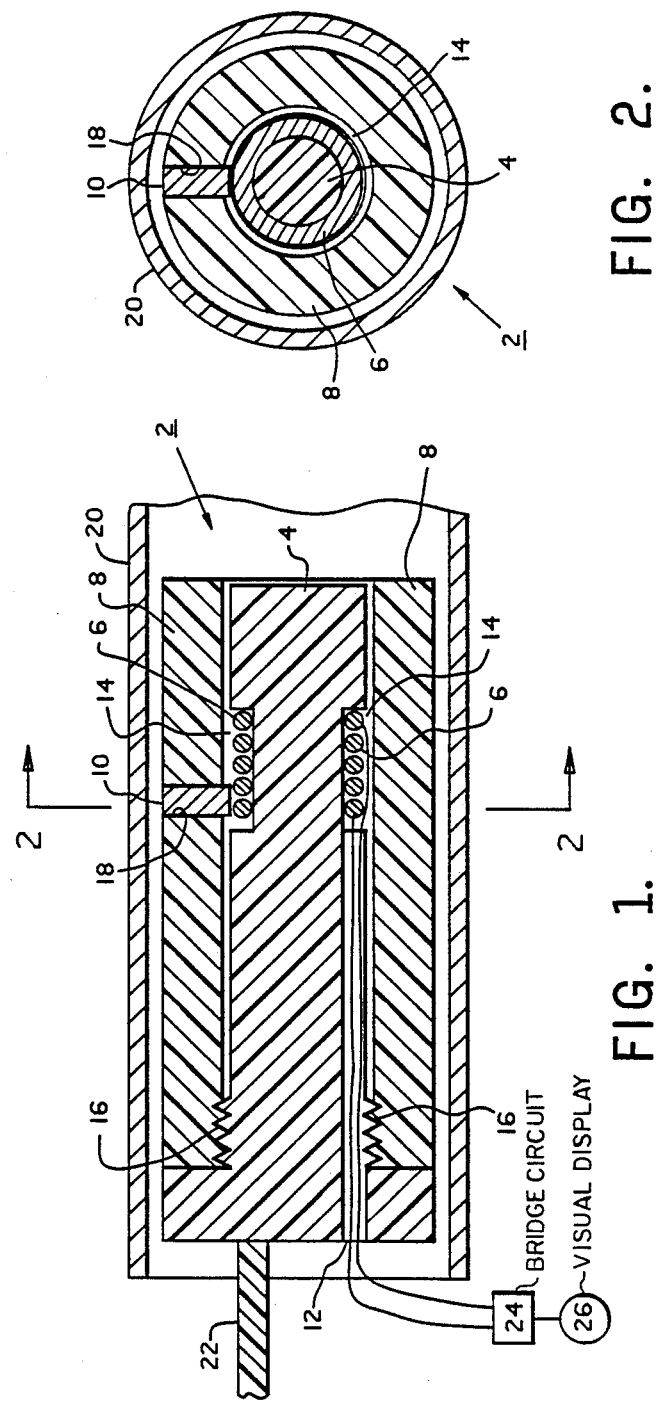

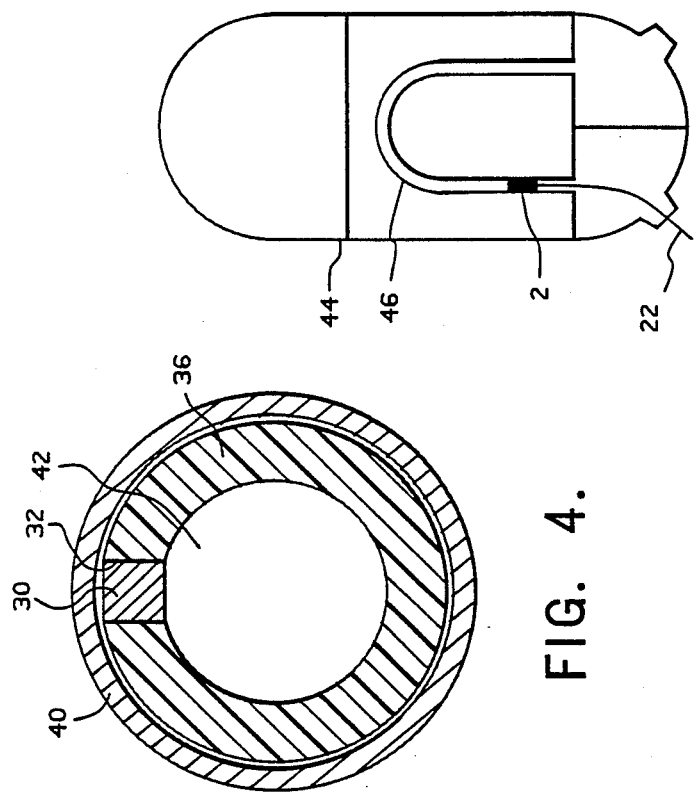
FIG. 17.
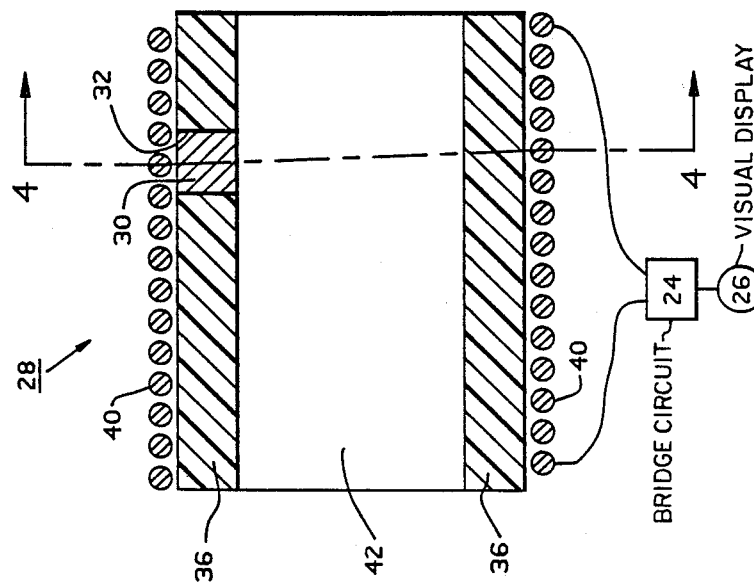
FIG. 4.
FIG. 3.

EDDY CURRENT APPARATUS INCLUDING CYLINDRICAL COIL WITH FLUX CONCENTRATOR FOR HIGH RESOLUTION DETECTION OF FLAWS IN CONDUCTIVE OBJECTS

BACKGROUND OF THE INVENTION

1. Field of the Invention

This invention relates to the detection of flaws in conductive objects, and more particularly, an improved eddy current flaw detector which isolates the precise location of flaws more accurately than prior art detectors.

2. Background Information

Non-destructive testing is used to test objects for flaws without damage to the object. In the case of the present invention, non-destructive testing of conductive objects is accomplished by inspecting for discontinuities by taking advantage of the object's ferro-magnetic and electrical conductivity properties.

The term "conductive object" is not intended to limit the class of testable objects to those typically used as electrical conductors, such as copper or aluminum. Rather, it is contemplated that the present invention could be used to test objects with limited electrical conductivity such as graphite.

When a coil of wire, through which alternating current is flowing, is placed in the vicinity of an object which is a good electrical conductor or has a high magnetic permeability, the impedance of the coil will change. If the coil is kept a fixed distance from the object and moved adjacent to the surface of the object the impedance of the coil will remain generally constant if the object is continuous. However, if the coil is moved in the vicinity of a discontinuity, such as a flaw, the coil's impedance will change from the value it assumed when out of the flaw's vicinity. It is that change in impedance which the present invention takes advantage of in operation.

A number of devices have been proposed for testing for flaws in conductive objects.

U.S. Pat. No. 4,507,610 discloses an apparatus for electromagnetically detecting flaws in metal objects which includes a coil of wire in which is disposed a split ring which is made of an electrically conductive material. Attached to the ends of the split ring is a sensing head which is used to couple the coil of wire to the metal object being tested. In use, the coil is excited with a high frequency electrical current which induces an electrical current in the closed circuit formed by the split ring and sensing head. When the sensing head is moved in the vicinity of a flaw, the impedance of the coil changes, thereby indicating the presence of a flaw. This device has the serious drawback of poor resolution due to the size and shape of the sensing head.

In addition to that device, a commonly used eddy current device, for the detection of flaws in nuclear plant steam generator tubing, is two tandem coils to provide a differential signal between the two coils. That apparatus, however, fails to provide distinct resolution which precisely locates the flaw in the metal, as it fails to provide angular resolution around tubular objects which are being tested. The employment of cross-wound coils is one variation of this device, however, they provide resolution sufficient to locate a flaw in only one hemicylinder of the sensor or the other.

Further, it has been known to shape the core of magnetic coils, to provide varying resolution patterns, when the core is to be used as the probe or sensor for the detection of flaws. For example, pointed ends have been formed on cores to provide more precise resolution. Also, other versions have horseshoe shaped cores which focus the flux at a desired point.

Also, it has been known to use two coils, a source coil and a detector coil, to detect flaws in conductive objects. With these devices, the source coil induces an electrical current in the detector coil and the detector coil's current is then monitored. When the detector coil is disposed in the vicinity of a flaw its impedance changes, thereby signalling the presence of a flaw. In some applications both coils are disposed on one side of the object while other applications require that the coils be placed on opposite surfaces of the object. The use of two coils requires more space, than those detectors which employ only one coil, and provides poor angular resolution. Also, in those applications requiring the coils to be disposed on opposite surfaces of the object, accessibility to both surfaces may be limited, restricting the amount of surface area which may be tested.

Therefore, despite the above-described devices there exists a real need for an improved electromagnetic sensor which is capable of pinpointing the location of flaws in conductive objects.

It is a primary object of the present invention to provide a device which is capable of accurately nondestructively locating flaws in conductive objects.

It is another object of the invention to produce a sensor which may be conveniently moved inside and along the longitudinal length of steam generator tubing in a nuclear steam supply system.

It is a further object of the invention to provide a sensor which is economical to manufacture and simple to operate.

It is yet another object of the present invention to provide a sensor which does not require the use of an external magnetic field to operate.

SUMMARY OF THE INVENTION

These and other objects are realized by a device which includes a coil of electrically conducting wire and an associated flux concentrator. The flux concentrator is disposed in contact with, or in close proximity to, the coil and may project radially outwardly from the outer surface of the coil, or radially inwardly from the inner surface of the coil. The flux concentrator magnetically couples a portion of the coil with a localized portion of the conductive object and is made from an electromagnetically active material such as, for example, ferrite or copper. By electromagnetically active it is meant that the material is a good electrical conductor and/or has a high magnetic permeaility. In the preferred form of the invention, the flux concentrator is disposed in a non-electromagnetically active spacer which fixes the distance between the coil and the test object while reducing direct coupling therebetween, and serves as a support for the flux concentrator.

In the preferred form of the invention, the spacer holds the flux concentrator in fixed relationship with respect to the coil. However, it is also anticipated that the spacer may be designed to rotate around the coil, thereby moving the flux concentrator around the perimeter of the coil. Additionally, it is anticipated that the spacer may be positioned in fixed relation with respect to the coil and designed to allow the flux concentrator to move relative to both the coil and spacer. Such arrangements would facilitate the testing of tubular members as they would allow the flux concentrator to move around the full perimeter of the member.

The ends of the coil's wire are connected to an electrical bridge circuit, which includes an associated alternating current electrical source, and a visual display means. A transport means, which may take the form of an elongated flexible rod, is also provided to move the sensor through conductive tubing when tubing is the object to be tested.

BRIEF DESCRIPTION OF THE DRAWINGS

FIG. 1 is a longitudinal section through a sensor in accordance with the teaching of the invention, which is disposed within tubing, and an associated bridge circuit and display means.

FIG. 2 is a cross section of the sensor of FIG. 1.

FIG. 3 is a longitudinal section through a second embodiment of a sensor according to the invention.

FIG. 4 is a cross section of the sensor of FIG. 3.

FIG. 17 is a schematic illustration of the invention as used to inspect the tubing in a nuclear steam supply system for flaws.

DESCRIPTION OF THE PREFERRED EMBODIMENTS

Figure 5:
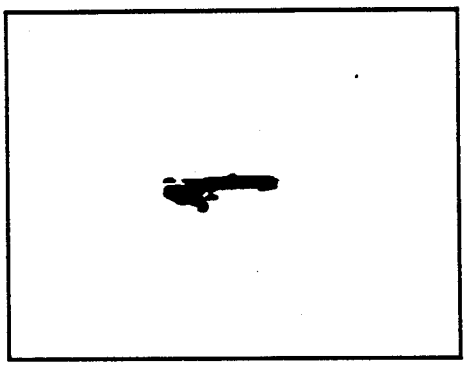
FIGS. 5-16 show lissajous patterns, as depicted on the display means, which show the reaction of the sensor of FIG. 1 to a conductive object and flaws therein.

FIGS. 1 and 2 show sensor 2 in accordance with the invention adapted for inspecting tubing 20 from the inside. Sensor 2 comprises support means 4, coil 6, spacer means 8, and flux concentrator 10. Support means 4 includes recess 14 which defines the location of coil 6 on support means 4, and passageway 12 through which the wire ends of coil 6 pass.

Sensor 2 is constructed by winding wire around support means 4, and within recess 14, to form coil 6. The number of turns of wire may be varied depending upon the desired amount of inductance of coil 6 and in the exemplary embodiment 60 turns of wire were used.

Spacer means 8 is then attached to support means 4. A convenient means of securing those two members together is through the employment of cooperating threads 16 Also, it is contemplated that suitable adhesives may be used to secure spacer means 8 to support means 4, thereby eliminating cooperating threads 16.

Spacer means 8 and support means 4 are preferably constructed of a non-electromagnetically active material such as "MICARTA" (trademark of the Westinghouse Electric Corporation). Spacer means 8 aids in properly spacing coil 6 from the conductive object to be tested. It is important that coil 6 be spaced from the object to be tested to reduce direct magnetic coupling between coil 6 and the object. Such magnetic coupling should occur primarily through flux concentrator 10 to provide proper resolution. Spacer means 8 is generally a hollow cylinder and includes opening 18 which receives flux concentrator 10.

Flux concentrator 10 is positioned adjacent or in contact with coil 6 in opening 18 and couples coil 6 with tubing 20. Although some direct coupling between coil 6 and the metal object will generally be present, that configuration helps to minimize such direct coupling. By coupling coil 6 with the conductive object through flux concentrator 10, only the small area of the object, in the vicinity of flux concentrator 10, is tested at any one particular time resulting in resolving the location where a flaw is present to a relatively small area; an area smaller than that provided by the entire coil.

The relative positioning between flux concentrator 10 and coil 6 is important also. Should flux concentrator 10 be disposed at too great a distance from coil 6 then close coupling between coil 6 and flux concentrator 10 will not occur. Alternatively, flux concentrator 10 may be mounted directly on coil 6 thereby providing the best possible coupling between flux concentrator 10 and coil 6.

In the exemplary embodiment, flux concentrator 10 is a cylindrical member; however, it may take on any one of a variety of shapes depending on the particular circumstances. For example, flux concentrator 10 could be ring shaped if it is desired to determine only the axial location of a flaw. Irrespective of the shape chosen though, the smaller the physical size of flux concentrator 10 the better the resolution of flaw detection that is achieved.

After emerging from passageway 12, the ends of the wire of coil 6 are connected to bridge circuit 24, which, in turn is electrically connected to visual display 26.

Transport means 22, in the form of a flexible rod, is attached to sensor 2 and moves sensor 2 through tubular member 20. In typical test situations, transport means 22 is rotated while, at the same time, moved along the longitudinal length of tubular member 20 to produce a helical-shaped search pattern. Although transport means 22 is shown as an elongated flexible rod in this Figure, other designs would function equally as well.

FIGS. 3 and 4 show an alternative embodiment of the sensor. Sensor 28 is constructed by forming coil 40 on spacer means 36. In this embodiment, flux concentrator 30 is disposed radially inwardly from coil 40 and extends through opening 32 in spacer means 36. It is important to note that in this embodiment, flux concentrator 30 is not shaped as a typical elongated magnetic core, but rather, is dimensionally small in relation to the longitudinal length of coil 40. Flux concentrator 30 couples coil 40 to the conductive object which is being tested and aids in varying the impedance of coil 40 in relation to the presence or absence of a flaw in the object. The ends of the wire of coil 40 are connected to bridge circuit 24, which, in turn, is electrically connected to visual display 26.

In this embodiment, the conductive object to be tested is placed within interior 42 of sensor 28. Such an arrangement is especially useful when testing the exterior of tubular members. The tube is placed within interior 42 and is then moved so that the entire surface area to be inspected passes in the vicinity of flux concentrator 30. Spacer means 36 serves to space coil 40 and flux concentrator 30 from the surface of the tubular member, as well as provide support for flux concentrator 30.

In use, sensor 2 is placed within the interior of tubular member 20, as shown in FIG. 1, and connected to bridge circuit 24 and display means 26. Power is then applied to bridge circuit 24. The power supply generates alternating current with a preferable frequency range of about 10 KHz to about 800 KHz. If the bridge circuit is balanced, then display means 26 would read generally zero. However, it is generally not possible to fully balance bridge circuit 24, therefore, some signal will always be present on display means 26. Such current is termed 'noise'. Also, varying amounts of noise are present as sensor 2 moves along a generally flawless conductive object as it is generally impossible to keep flux concentrator 10 a precise, fixed distance from surface of the conductive object which is to be tested, as it is moved.

When sensor 2 is first placed within tubular member 20 it is necessary that bridge circuit 24 be balanced as placing sensor 2 in the vicinity of tubular member 20 causes the impedance of coil 6 to change. The amount of impedance change of coil 6 varies depending upon composition, resistivity, magnetic permeability, thickness, and other properties of tubular member 20. Therefore, it is necessary that bridge circuit 24 be rebalanced before each use.

After sensor 2 has been placed within tubular member 20, and bridge circuit 24 has been balanced, transport means 22 then moves sensor 2 within the interior of tubular member 20. Typically, sensor 2 would be rotated as it is moved along the longitudinal axis of tubular member 20 producing a helical search pattern. If it is desired to test only a longitudinal portion of a pipe, such as a seam, sensor 2 need not be rotated.

As a third alternative, sensor 2 may be moved along the longitudinal axis of tubular member 20, stopped, and rotated around a cross section of tubular member 20. This process would be repeated again and again until the entire surface of tubular member 20 is inspected.

As long as flux concentrator 10 encounters no discontinuities in tubular member 20, the bridge circuit will remain generally balanced, resulting in a zero output from the display means, except for noise. However, when flux concentrator 10 is adjacent a flaw in tubular member 20, the impedance of coil 6 will change. That change in impedance results in bridge circuit 24 becoming unbalanced causing display means 26 to generate a well-known lissajous pattern.

EXAMPLES

As specific examples of the invention, a coil of 26 gauge wire, 0.475 inches in diameter and 0.375 inches long, with 59 turns, was formed around a "MICARTA" support means, and a "MICARTA" cylinder with an outer diameter of 0.75 inches, an inner diameter of 0.50 inches and a wall thickness of 0.125 inches, was positioned around the coil and support means to serve as a spacer means. The "MICARTA" cylinder had formed in its surface a 0.11 inch diameter hole to mount the flux concentrator and was threaded at one end to engage the support means.

A small cylinder of solid copper, approximately 0.125 inches long with a diameter of about 0.1 inches was used as the flux concentrator and was placed in the hole of the "MICARTA" sleeve. The sensor used in these examples is the one illustrated in FIG. 1. The coil was connected to a Nortec 25-L eddy current flaw detector. The power source was set to 500 KHz and a storage type oscillograph, with 90× equal magnification in both the horizontal and vertical axes, was attached to the Nortec 25-L detector and served as the display means.

A ⅝-inch inconel steam generator section of tubing, with a nominal thickness of 0.055 inches, was used as the metal object to be tested. A flaw was simulated by drilling an approximately 0.1875 inch hole all the way through the tube's wall about 1.25 inches from one end of the tube's longitudinal axis. The sensor was placed inside the tube and the bridge circuit was balanced. The tube was then rotated around the sensor and the oscillograph display was viewed. A lissajous pattern, depicted in general as FIG. 5, was generated. As that portion of the tube was generally continuous and without flaws, the displayed pattern represented noise.

Figure 6:
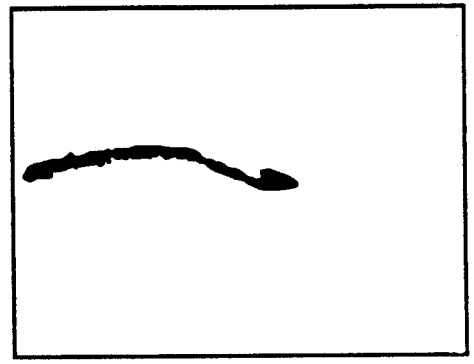

Next, the sensor was moved so that the flux concentrator passed by the drilled hole. FIG. 6 shows the general lissajous pattern which was displayed on the storage type oscillograph as the flux concentrator passed the hole. The pattern shown on the oscillograph plots the amplitude and phase angle of the voltage across the bridge circuit. The trace extended in a direction generally to the left of the calibration point.

Figure 7:
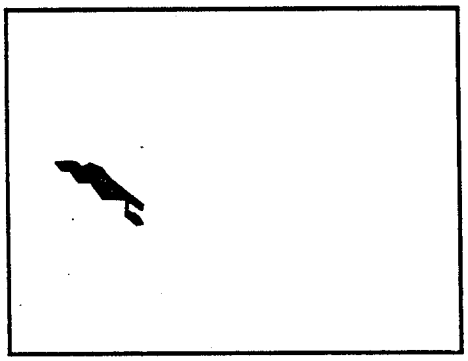
Figure 8:
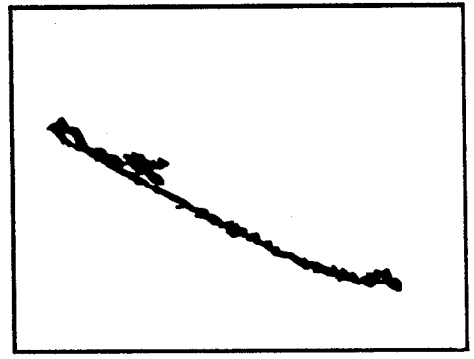

The copper flux concentrator was then replaced by a cylinder of ferrite with an outer diameter of about 0.125 inches, an inner diameter of about 0.031 inches and a length of about 0.125 inches. The ferrite cylinder happened to be hollow, However, solid ferrite could also have been used. The bridge circuit was again balanced and the sensor was rotated to determine the general noise level present. That noise is shown generally in FIG. 7. The sensor was then moved so that the flux concentrator passed by the hole. FIG. 8 shows the oscillograph display. It is significant to note that the oscillograph trace extended generally to the right and downward from the calibration point when using a ferrite flux concentrator while, with a copper flux concentrator, the lissajous trace extended generally horizontally to the left, illustrating a difference in phase angle across the bridge when using ferrite rather than copper as a flux concentrator.

Figure 9:
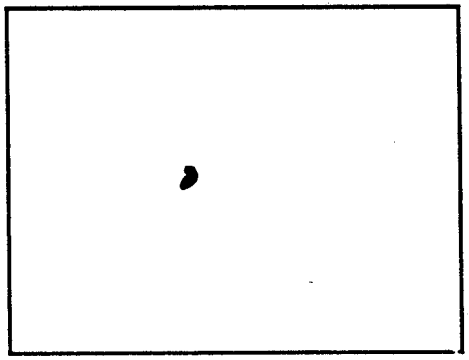
Figure 10:
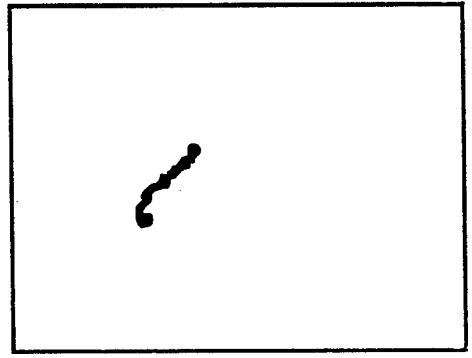

The experiment was repeated using varying frequencies of supply current. FIGS. 9 and 10 show, respectively, the noise using a copper flux concentrator and the lissajous trace patterns as the flux concentrator passed by the hole with 50 KHz supply current. The pattern of FIG. 9 extends generally downward and to the left.

Figure 11:
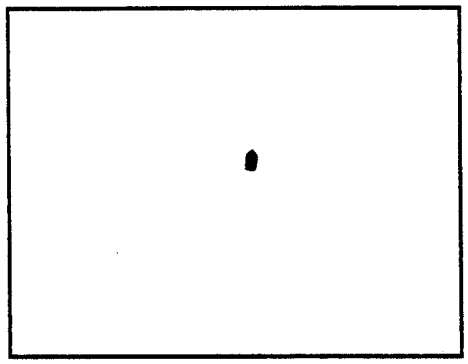
Figure 12:
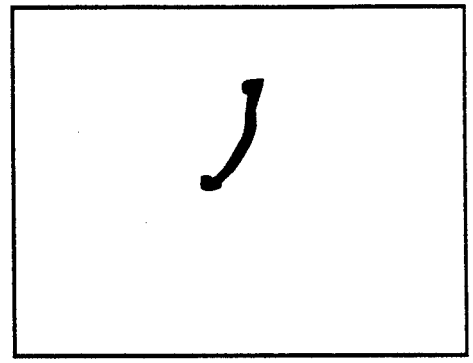

FIGS. 11 and 12 show, respectively, the noise and lissajous trace patterns, using a 50 KHz supply current, with a ferrite flux concentrator. The trace pattern of FIG. 11 extends generally upwardly and slightly to the right.

Figure 13:
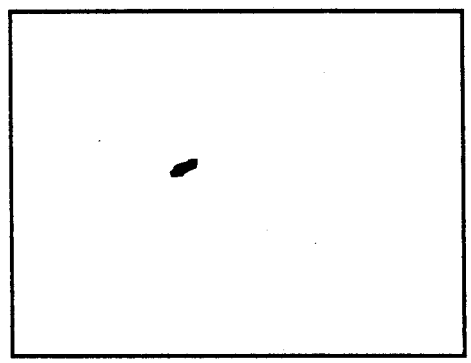
Figure 14:
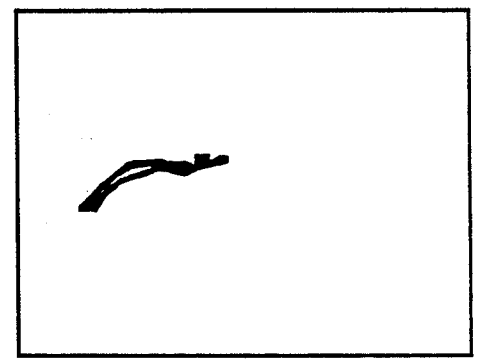

FIGS. 13 and 14 show, respectively, the noise and lissajous trace pattern using the copper flux concentrator with a power supply of 200 KHz. The trace pattern of FIG. 13 extends generally to the left and downward.

Figure 15:
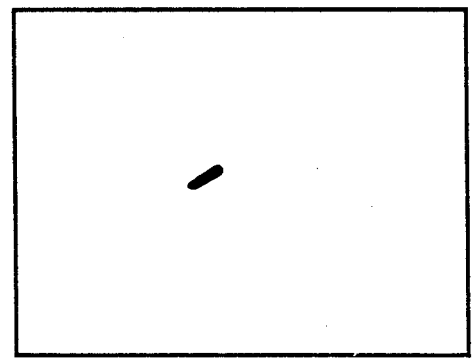
Figure 16:
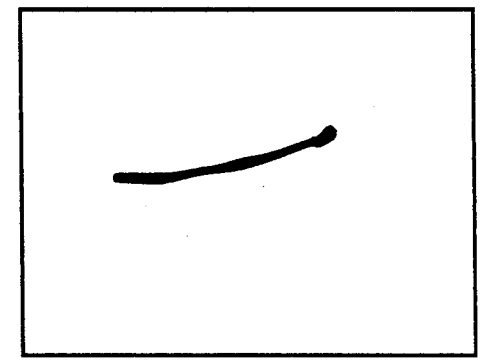

FIGS. 15 and 16 show the respective noise and lissajous trace patterns with a 200 KHz supply current using the ferrite flux concentrator. The FIG. 16 trace pattern extends generally to the right and upward.

The above-recited examples demonstrate that the method and apparatus of the present invention are effective in isolating the location of flaws in conductive objects.

The invention is particularly suitable, as shown in FIG. 17, for inspecting the tubing in the steam generator 44 of a nuclear steam supply system of a pressurized water reactor. Such a steam generator 44 has thousands of U-shaped tubes 46 which can be inspected for flaws by inserting the detector 2 in one end of each such tube (only one shown for clarity) and analyzing any changes in the impedance of the detector coil as it passes through the tubing.

Whereas particular embodiments of the invention have been described for purposes of illustration, it will be evident to those skilled in the art that numerous variations of the details may be made without departing from the invention as defined in the appended claims.

What is claimed is:

1. A sensor for detecting flaws in conductive objects comprising:
   a single cylindrical coil of electrically conducting wire which generates a magnetic flux in response to a coil current applied thereto, and
   flux concentrator means comprising a piece of electromagnetically active material disposed in close proximity to and extending only radially from the cylindrical surface of said coil to the conductive object to provide close coupling for said magnetic flux between only a portion of said coil and the object, and to space the remainder of the cylindrical coil from the object such that flaws in the object adjacent the flux concentrator produce a change in the flux and hence a change in coil current indicative of flaw detection, said flux concentrator being dimensionally small in relation to the longitudinal length of the cylindrical coil and being sized and shaped to provide a desired resolution of flaw detection.

2. Apparatus for detecting flaws in conductive objects comprising:
   a sensor comprising a single cylindrical coil of electrically conducting wire which generate a magnetic flux in response to an electrical current flowing through, and flux concentrator means comprising a piece of electromagnetically active material disposed in close proximity to and extending only radially from the cylindrical surface of said coil to the conductive object to provide close coupling for said magnetic flux between only a portion of said coil and the object and to space the remainder of the cylindrical coil from the object, such that flaws in the object adjacent the flux concentrator produce a change in the flux and hence a change in coil current indicative of flaw detection, said flux concentrator being dimensionally small in relation to the longitudinal length of the cylindrical coil and being sized and shaped to provide a desired resolution of flaw detection, and
   means connected to said coil for indicating a change in impedance of said coil from said change in current.

3. The apparatus of claim 2 including electromagnetically inactive spacer means for spacing said cylindrical coil radially a predetermined distance from the object, said flux concentrator extending radially through said spacer and in close proximity with both said coil and said object.

4. The apparatus of claim 3 wherein said spacer means comprises "MICARTA".

5. The apparatus of claim 3 wherein said flux concentrator means comprises ferrite.

6. The apparatus of claim 3 wherein said flux concentrator means includes copper.

7. The apparatus of claim 3 wherein said flux concentrator means is disposed radially outwardly from said coil.

8. The apparatus of claim 3 wherein said spacer means and said flux concentrator means are disposed radially inwardly from said coil.

9. Apparatus for testing for flaws in the tubing of a nuclear steam supply system steam generator said apparatus comprising:
   a detector, insertable in said tubing, and comprising a cylindrical support means, a single cylindrical coil of electrically conducting wire which generates a magnetic flux in response to a current applied thereto wound on said support means, a cylindrical spacer means surrounding said coil, and flux concentrator means comprising a piece of electromagnetically active material supported by said spacer means and disposed in close proximity to and extending only radially outwardly from the cylindrical surface of said coil to the tubing to provide close coupling for said magnetic flux between a portion of said coil and the tubing such that flaws in the tubing adjacent said flux concentrator produce a change in the flux and hence a change in coil current indicative of flaw detection, said flux concentrator means being dimensionally small in relation to the longitudinal length of the cylindrical coil and being sized and shaped to provide a desired resolution of flaw testing of the tubing, and
   means connected to said coil for indicating a change in impedance of said coil from said change in current.

10. The apparatus of claim 9 including transport means for moving said detector through the tubing.

11. The apparatus of claim 10 wherein said spacer means comprises "MICARTA".

12. The apparatus of claim 10 wherein said flux concentrator means comprises ferrite.

13. The apparatus of claim 10 wherein said flux concentrator means includes copper.

* * * * *